United States Patent
Patton

(10) Patent No.: US 11,224,701 B1
(45) Date of Patent: Jan. 18, 2022

(54) SINGLE DOSE DISPOSABLE SYRINGE WITH NEEDLE PROTECTOR

(71) Applicant: Jarvis Patton, Birmingham, AL (US)

(72) Inventor: Jarvis Patton, Birmingham, AL (US)

( * ) Notice: Subject to any disclaimer, the term of this patent is extended or adjusted under 35 U.S.C. 154(b) by 13 days.

(21) Appl. No.: 16/547,000

(22) Filed: Aug. 21, 2019

(51) Int. Cl.
*A61M 5/32* (2006.01)
*A61M 5/50* (2006.01)
*A61M 5/28* (2006.01)

(52) U.S. Cl.
CPC ............ *A61M 5/50* (2013.01); *A61M 5/3202* (2013.01); *A61M 5/326* (2013.01); *A61M 5/3234* (2013.01); *A61M 5/282* (2013.01)

(58) Field of Classification Search
CPC .. A61M 5/321; A61M 5/3243; A61M 5/3271; A61M 5/3272; A61M 5/3257
See application file for complete search history.

(56) References Cited

U.S. PATENT DOCUMENTS

| | | | |
|---|---|---|---|
| 1,480,449 A | | 1/1924 | Kendall |
| 4,170,993 A | | 10/1979 | Alvarez |
| 4,425,120 A | | 1/1984 | Sampson et al. |
| 4,643,199 A | | 2/1987 | Jennings, Jr. et al. |
| 4,693,708 A | | 9/1987 | Wanderer et al. |
| 4,702,738 A | | 10/1987 | Spencer |
| 4,723,943 A | | 2/1988 | Spencer |
| 4,840,185 A | * | 6/1989 | Hernandez .......... A61M 5/3271 600/576 |
| 4,966,592 A | * | 10/1990 | Burns ................. A61M 5/3271 604/198 |
| 5,851,078 A | | 12/1998 | Bow et al. |
| 6,379,337 B1 | * | 4/2002 | Mohammad M. B. B. S. ............ A61M 5/322 604/162 |
| 6,547,764 B2 | * | 4/2003 | Larsen ................. A61M 5/326 604/110 |
| 9,603,434 B2 | | 3/2017 | Zhu et al. |
| 9,907,916 B2 | | 3/2018 | Evans |
| 9,962,497 B2 | | 5/2018 | Takemoto |
| 10,004,854 B2 | | 6/2018 | Evans et al. |
| 2013/0011175 A1 | | 1/2013 | Hefetz et al. |
| 2015/0164202 A1 | | 6/2015 | Zhu et al. |

* cited by examiner

*Primary Examiner* — Laura A Bouchelle
(74) *Attorney, Agent, or Firm* — Lanier Ford Shaver & Payne, PC; Gerald M. Walsh

(57) ABSTRACT

This invention is a syringe having a tubular sleeve protector. The syringe has a barrel with an injection needle and a guide pin on an exterior surface of the barrel. The barrel and the injection needle are in an interior of a tubular sleeve has a spiral guide track on an interior wall. The guide pin fits in the spiral guide track and moves the barrel towards a bottom end of the tubular sleeve as the barrel is rotated, thereby extending the injection needle out of the tubular sleeve. A lateral guide track connects the spiral guide track to a vertical guide track. The guide pin moves from the bottom of the spiral guide track through the lateral guide track to the vertical guide track when the syringe barrel is further rotated. The injection needle is retracted into the interior of the tubular sleeve when the guide pin is moved into the vertical guide track and moved upwards in the vertical guide track towards a top end of the tubular sleeve.

30 Claims, 4 Drawing Sheets

SINGLE DOSE DISPOSABLE SYRINGE WITH NEEDLE PROTECTOR

FIELD OF THE INVENTION

This invention relates to tubular sleeves on syringes for covering and protecting injection needles prior to use wherein the barrel of the syringe can be pushed and pulled slideably in the tubular sleeve to advance the injection needle out of the tubular sleeve and to retract the injection needle back into the tubular sleeve, respectively. More particularly, this invention relates to a tubular sleeve constructed to advance and retract an injection needle on a syringe from the tubular sleeve by irreversible rotation in one direction of the syringe barrel within the tubular sleeve.

BACKGROUND OF THE INVENTION

Various forms of protective sleeves for hypodermic injection needles are known. See U.S. Pat. Nos. 4,170,993; 4,425,120; 4,693,708; 4,702,738; 4,723,943; and 4,966,592. All of these devices use linear tracks on an internal surface of a sheath or sleeve which fits slidably and rotatably around the barrel of a syringe and around an injection needle at the tip of the barrel. The barrel of the syringe is pushed or pulled linearly along the track relative to the sleeve or the sleeve is pushed or pulled linearly along the track relative to the barrel of the syringe to extend or withdraw the injection needle from the sleeve. The syringe barrel is rotatable relative to the sleeve so that the syringe barrel can be rotated to lock and unlock the syringe barrel at desired positions along the length of the sleeve. These devices have relatively complex structures and require relatively complex movements to extend the injection needle out of the sleeve and to withdraw the injection needle into the sleeve.

SUMMARY OF THE INVENTION

The present invention provides a single dose disposable syringe having a tubular sleeve protector. The syringe has a syringe barrel, a plunger, and an injection needle attached to the syringe barrel. A guide pin is attached to an exterior surface of the syringe barrel. The syringe barrel and the injection needle are positioned inside an interior of a tubular sleeve. The tubular sleeve has a spiral guide track on an interior wall of the tubular sleeve. The guide pin is constructed to fit in the spiral guide track and to move the syringe barrel towards a bottom end of the tubular sleeve as the syringe barrel is rotated, relative to the tubular sleeve, in the direction of the spiral guide track, from a top end of the spiral guide track to a bottom end of the spiral guide track. The injection needle is thereby extended out of the bottom end of the tubular sleeve. A lateral guide track on the interior wall of the tubular sleeve connects the spiral guide track to a vertical guide track on the interior wall of the tubular sleeve. The guide pin is constructed to move from the spiral guide track through the lateral guide track to the vertical guide track when the syringe barrel is further rotated in the direction of the spiral guide track. The injection needle is retracted into the interior of the tubular sleeve when the guide pin is moved into the vertical guide track and moved upwards in the vertical guide track towards a top end of the tubular sleeve.

A retaining slot is located at a first end (top end) and at a second opposite end (bottom end) of the spiral guide track and at a top end of the vertical track to retain the guide pin. A biasing member is located on the injection needle to bias the guide member upwards in the vertical guide track. The guide pin in the spiral guide track moves from the top end of the spiral guide track to the bottom end of the spiral guide track. The retaining slot at the bottom end of the spiral guide track is constructed to prevent a reverse in rotation of the syringe barrel.

A method of protecting a syringe needle on a single dose disposable syringe is also provided. The method includes extending the syringe needle out from a bottom end of the tubular sleeve by rotating the syringe barrel, relative to the tubular sleeve, in the direction of the spiral guide track and moving the guide pin from a top end of the spiral guide track to a bottom end of the spiral guide track. The method further includes retracting the injection needle back into the tubular sleeve by further rotating the syringe barrel, relative to the tubular sleeve, in the direction of the spiral guide track and by moving the guide pin across the lateral guide track and into the vertical guide track and moving the guide pin upwards in the vertical guide track towards the top end of the tubular sleeve, thereby moving the syringe barrel and syringe needle towards the top end of the tubular sleeve.

An advantage of the present invention is the ability to extend the injection needle from the protective tubular sleeve with a single rotation of the syringe barrel.

Another advantage is the ability to retract the injection needle back into the tubular housing with a single rotation of the syringe barrel.

Another advantage is a disposable syringe with a needle protector that is simple in construction, easy to use, and relatively inexpensive to manufacture.

DETAILED DESCRIPTION OF THE INVENTION

While the following description details the preferred embodiments of the present invention, it is to be understood that the invention is not limited in its application to the details of arrangement of the parts as shown in the figures or to the steps of the methods disclosed herein, since the invention is capable of other embodiments and of being practiced in various ways.

Figure 1:
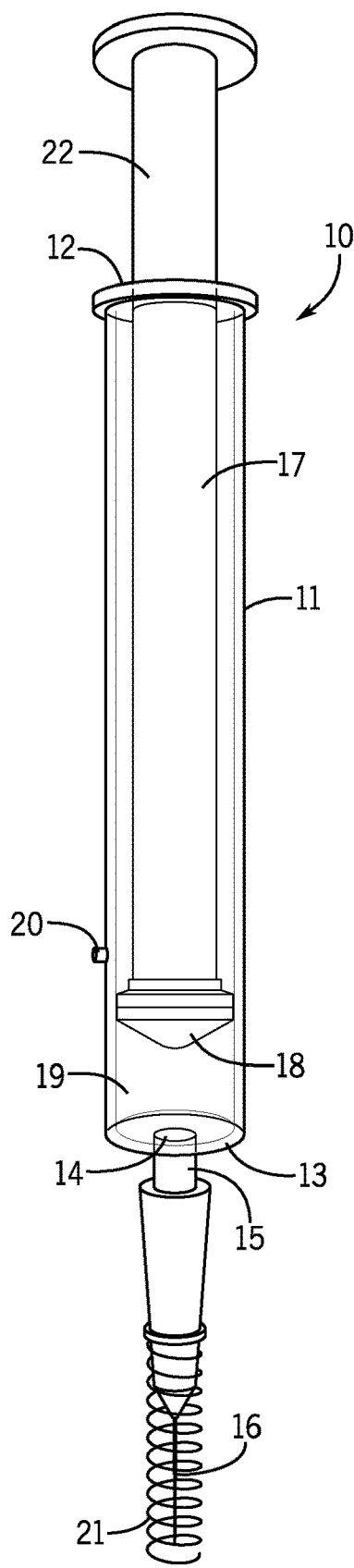
FIG. 1 shows a perspective side view of an exemplary syringe of the present invention.

FIG. 1 shows a perspective side view of an exemplary syringe 10 of the present invention, shown as a single dose disposable syringe. The syringe 10 has a barrel 11 with a top end 12 and a bottom end 13. The bottom end 13 has an opening 14 into a nipple 15 extending from the bottom end 13. An injection needle 16 is attached to the nipple 15 by methods well known in the art. The needle 16 has a biasing member, such as a spring 21, attached thereto. A plunger 17 has a handle 22 and a tip 18 which is in the interior of the syringe barrel 11. A prefilled dose of drug for injection 19 is shown in the interior of the syringe barrel 11 between the plunger tip 18 and the bottom 13 of the syringe barrel 11. A guide pin 20 is shown attached to the exterior side of the syringe barrel 11. The guide pin 11 is constructed for use with guide tracks on the internal wall of a tubular sleeve 30 as described below.

Figure 2:
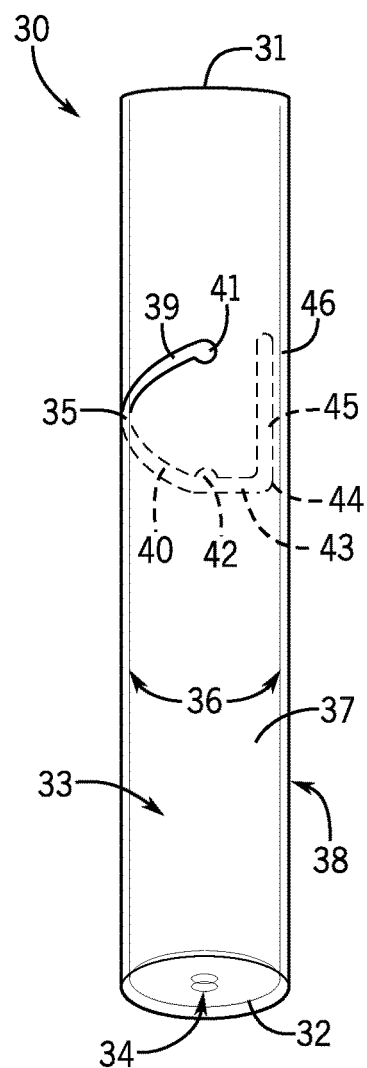
FIG. 2 shows a side view of a tubular sleeve of the present invention.

FIG. 2 shows a side view of a tubular sleeve 30 of the present invention. The tubular sleeve 30 has a top end 31, a bottom end 32, and an interior 33. The bottom end 32 is closed except for an opening 34 through which needle 16 can pass. The syringe barrel 11 does not pass through end 32 of the tubular sleeve 30. Top end 31 of the tubular sleeve 30 is open. A spiral guide track 35 is shown on an interior wall 36 of the tubular sleeve 30 and is shown in FIG. 2 from a first side 37 of the tubular sleeve as a solid line 39 and as a dashed line 40 on a second opposite side 38. Spiral guide track 35 starts at its top end with a first retaining slot 41 and extends downward along solid line 39 on the first side 37 of the tubular sleeve 30. Spiral guide track 35 then spirals around the interior wall 36 along dashed line 40, on the second opposite side 38, and has a second retaining slot 42 at its bottom end. The guide track then continues as a horizontal guide track, shown by dashed line 43, along the interior wall 36 to a vertical guide track. The vertical guide track, shown by dashed line 45, extends towards the top end 31 of the tubular sleeve 30 and terminates with a third retaining slot 46 at its top end.

Figure 3:
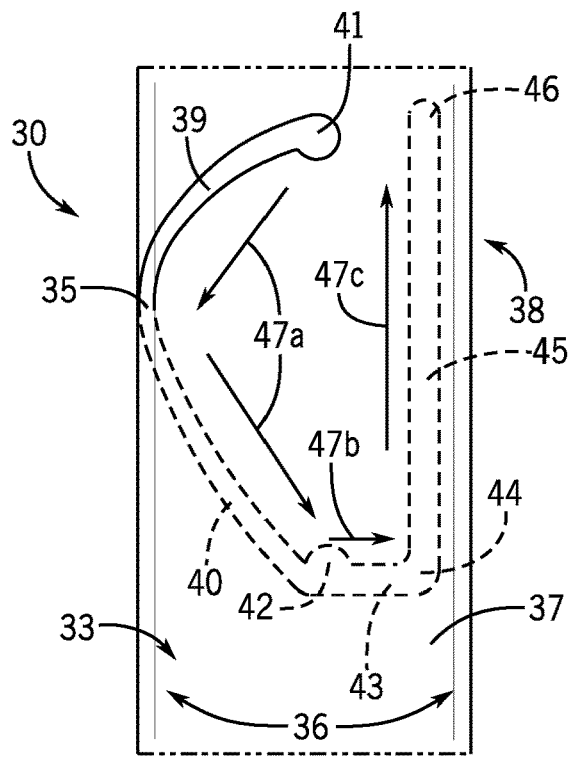
FIG. 3 shows an enlarged view of a guide track on an inner wall of the tubular sleeve seen from a first side of the tubular sleeve.
Figure 4:
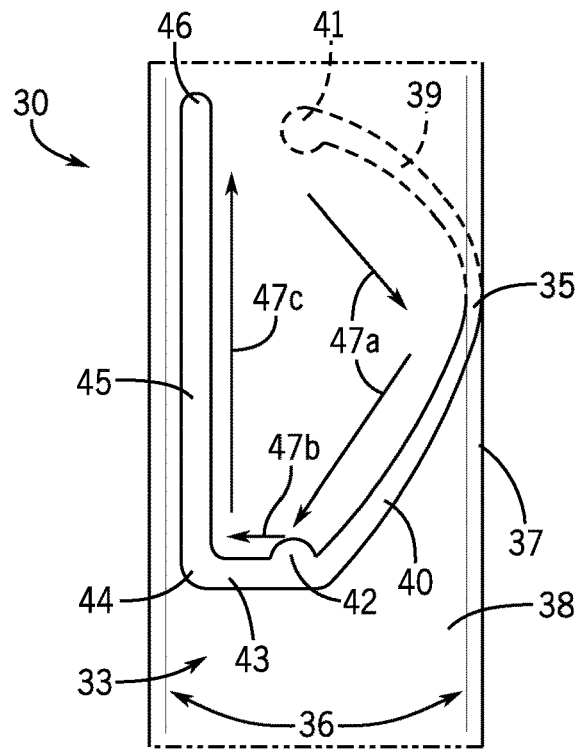
FIG. 4 shows an enlarged view of a guide track on an inner wall of the tubular sleeve seen from a second opposite side of the tubular sleeve.

FIG. 3 shows an enlarged view of the spiral guide track 35, the horizontal guide track 43, and the vertical guide track 45, shown from the first side 37 of the tubular sleeve 30. The retaining slots 41 and 42 reversibly retain the guide pin 20. Arrows 47a, 47b, and 47c show the direction of travel of the guide pin 20 along the guide tracks 35, 43, and 45 as the guide pin 20 travels along the guide tracks by rotation of the barrel 11 relative to the tubular sleeve 30. FIG. 4 shows an enlarged view of the spiral guide track 35, the horizontal guide track 43, and the vertical guide track 45, shown from the second opposite side 38 of the tubular sleeve 30. The guide tracks on the second opposite side 38 are shown in solid lines and the portion 38 of the guide track on the first side 37 is shown in a dashed line.

Figure 5:
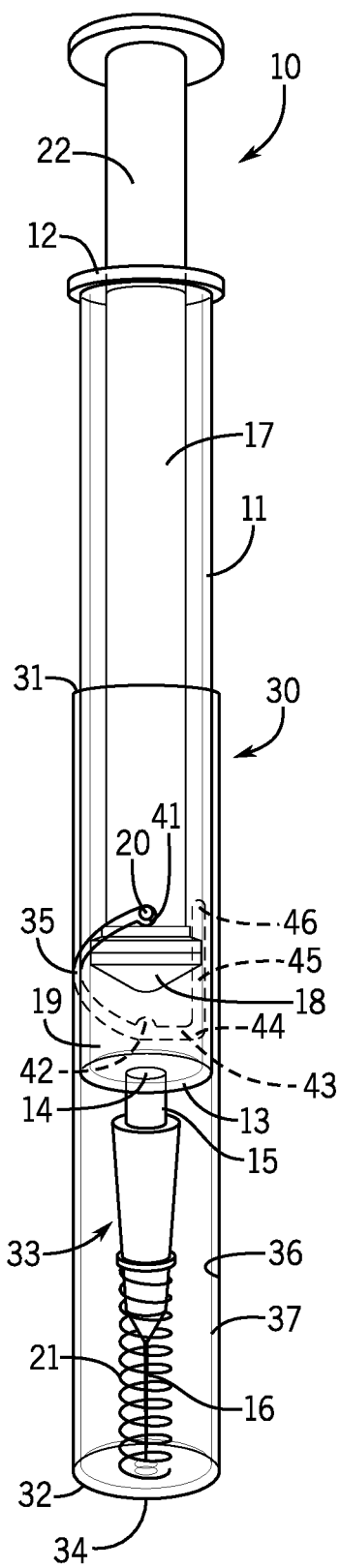
FIG. 5 shows a perspective side view of the syringe inserted into the tubular sleeve in a first position in the guide track with the injection needle enclosed within the tubular sleeve.

FIG. 5 shows a view of the first side 37 of the syringe 10 inserted into the tubular sleeve 30 in a pre-use configuration. The injection needle 16 is enclosed within the tubular sleeve 30. The guide pin 20 is positioned in the first retaining slot 41. A prefilled dose of drug for injection 19 is shown between the plunger tip 18 and the bottom 13 of the barrel 11. By rotating the syringe barrel 11 in the same direction as the spiral guide track 35 the guide pin 20 can be moved out of the first retaining slot 41 and advanced down the spiral guide track 35, indicated by arrows 47a shown in FIGS. 3 and 4.

Figure 6:
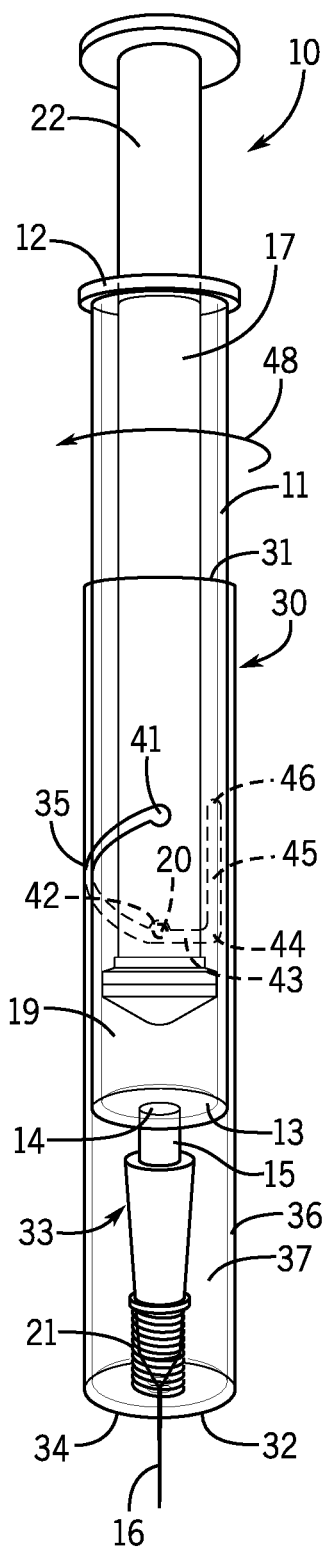
FIG. 6 shows a perspective side view of the syringe inserted into the tubular sleeve and rotated into a second position in the guide track with the injection needle extended out of the tubular sleeve for use.

FIG. 6 shows that the guide pin 20 has been rotated into the second retaining slot 42 of the spiral guide track 35. The rotation of the barrel 11 to the second position has caused the barrel 11 to move downward in the tubular sleeve 30 so that the needle 16 extends out of the tubular sleeve 30 through the opening 34 in the bottom end 32 of the tubular sleeve 30. The downward movement of the barrel 11 has also caused the spring 21 to become compressed so that the syringe 10 is biased in an upward direction towards the top end 31 of the tubular sleeve 30. The syringe 10 as shown in FIG. 6 is in a for-use configuration and the drug dosage in the syringe 10 can be injected as prescribed by pushing the handle 22 of the plunger 17 to force the tip 18 of the plunger 17 to the bottom 13 of the barrel 11, as is known in the art.

Figure 7:
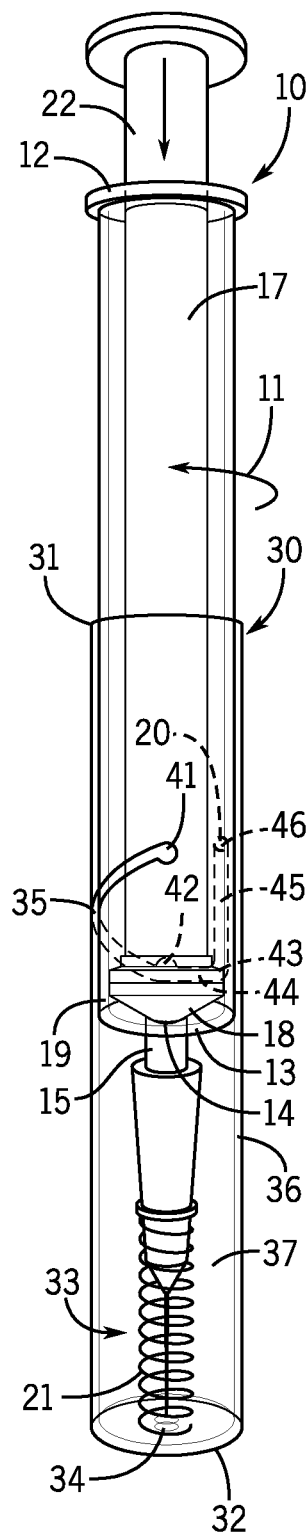
FIG. 7 shows a perspective side view of the syringe inserted into the tubular sleeve and rotated into a third position in the guide track with the injection needle retracted back into the tubular sleeve after use and ready for disposal.

After injection of the drug dosage the barrel 11 can be rotated again, as illustrated in FIG. 7, to move the guide pin 20 laterally along the horizontal guide track 43, shown by arrows 47b (FIG. 3 and FIG. 4) until it engages the vertical guide track 45. When the guide pin 20 enters the vertical guide track 45 as a result of rotating the barrel 11, the syringe 10 is free to move upward, shown by arrows 47c (FIG. 3 and FIG. 4) and the force of the compressed spring 21 will cause guide pin 20 to move upward until the guide pin 20 enters the third retaining slot 46 at the top of the vertical guide track 45. The injection needle 16 is then retracted back into the tubular sleeve 30. The syringe 10 is in an after-use configuration and is ready for disposal.

Figure 8:
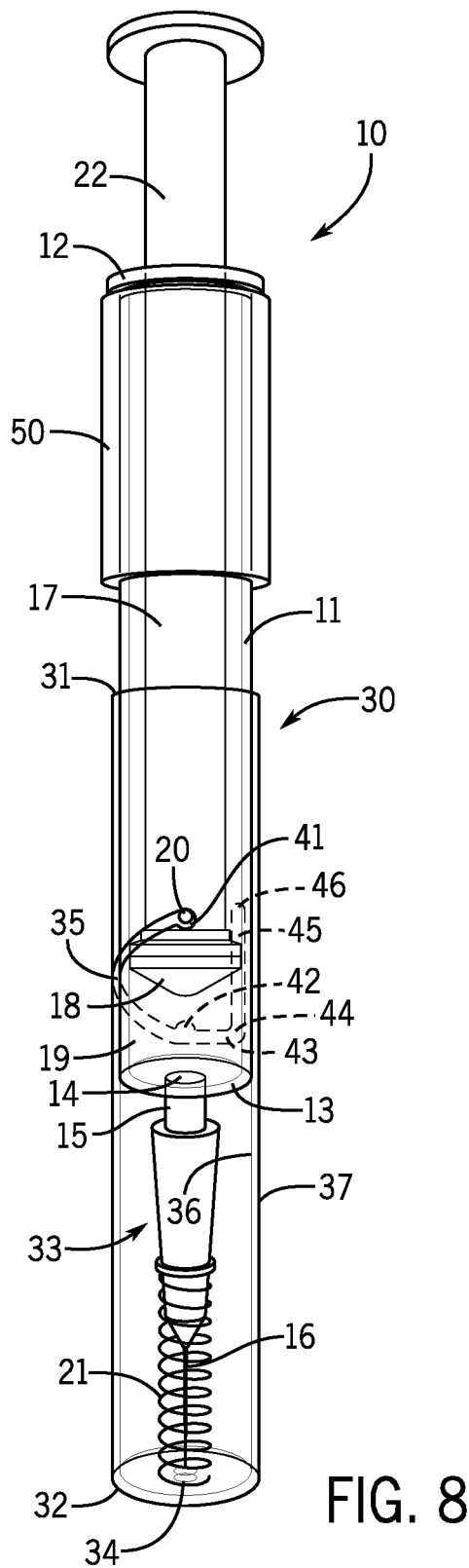
FIG. 8 shows a perspective side view of the syringe having a finger grip on the syringe barrel to facilitate rotation of the syringe barrel.

FIG. 8 shows the syringe 10 having a finger grip 50 on the barrel 11 at the top end 12 to facilitate rotation of the barrel 11. The finger grip 50 has, preferably, the same diameter as the tubular sleeve 30. The finger grip 50 can be made of any suitable plastic or rubber or a combination thereof and have a ribbed or roughened surface to facilitate gripping and prevent slippage.

The second retaining slot is constructed, preferably, to seat the guide pin with a snap-like effect and with sufficient resistance for the guide pin to remain in the retaining slot, even with the spring compressed. However, the second retaining slot is also constructed so that the guide pin can be moved out of the second retaining slot with rotation of the barrel. The second retaining slot is further constructed, preferably, to prevent counter rotation of the barrel in an attempt to move the guide pin in an opposite direction along the spiral guide track. Once the guide pin enters the third retaining slot the guide pin, preferably, cannot be moved out of the third retaining slot.

The present invention provides a method of protecting a syringe needle on a single dose disposable syringe. A syringe having a syringe barrel, a plunger, and an injection needle is provided. Also provided is a guide pin on an exterior surface of the syringe barrel. The syringe barrel and injection needle are positioned inside a tubular sleeve so that the injection needle is protected. The tubular sleeve has a spiral guide track, a lateral guide track, and a vertical guide track on an interior wall of the tubular sleeve. The guide pin can fit into the spiral guide track, the lateral guide track, and the vertical guide track.

In order to use the syringe, the syringe needle must be extended out from a bottom end of the tubular sleeve. This is accomplished by rotating the syringe barrel, relative to the tubular sleeve, in the direction of the spiral guide track and by moving the guide pin from a top end of the spiral guide track to a bottom end of the spiral guide track, thereby moving the syringe barrel and injection needle towards the bottom end of the tubular sleeve. In this configuration, with the needle extended out of the tubular sleeve, the syringe is ready for use and a dosage in the syringe may be injected into a patient using the plunger.

In order to continue protecting the injection needle after use, the injection needle must be retracted back into the tubular sleeve. This is accomplished by further rotating the syringe barrel, relative to the tubular sleeve, in the direction of the spiral guide track and by moving the guide pin across the lateral guide track and into the vertical guide track. Once the guide pin is in the vertical guide track it is moved upwards in the vertical guide track towards the top end of the tubular sleeve, thereby moving the syringe barrel and syringe needle towards the top end of the tubular sleeve. The needle is, thus, retracted back into the tubular sleeve.

The foregoing description has been limited to specific embodiments of this invention. It will be apparent, however, that variations and modifications may be made by those skilled in the art to the disclosed embodiments of the invention, with the attainment of some or all of its advantages and without departing from the spirit and scope of the present invention. For example, the tubular sleeve can be made out of any suitable plastic or metal or a combination thereof. The guide pin and retaining slots can have various shapes or designs and still produce equivalent functions described herein. The tubular sleeve of the present invention can be adapted for any type of syringe. Any suitable type of biasing member, in addition to the spring, may be used. The tubular sleeve can also be used without a biasing member by a user pulling the syringe barrel towards the top end of the tubular sleeve after the guide pin has been rotated into the vertical guide track. Although the syringe barrel is described as being rotated relative to the tubular sleeve it is equivalent to rotating the tubular sleeve relative to the syringe barrel.

It will be understood that various changes in the details of the method and materials which have been described and illustrated above in order to explain the nature of this invention may be made by those skilled in the art without departing from the principle and scope of the invention as recited in the following claims.

I claim:

1. A single dose disposable syringe having a tubular sleeve protector, said syringe comprising:
   a) a syringe barrel, a plunger, and an injection needle attached to the syringe barrel;
   b) a guide pin on an exterior side of the syringe barrel;
   c) the syringe barrel and the injection needle positioned in an interior of a tubular sleeve, the tubular sleeve having a first side and a second side radially opposite the first side;
   d) the tubular sleeve having a spiral guide track on an interior wall of the tubular sleeve, the spiral guide track making only a single spiral turn from the first side to the second side on the interior wall of the tubular sleeve;
   e) the guide pin constructed to fit in the spiral guide track and to move the syringe barrel towards a bottom end of the tubular sleeve as the syringe barrel is rotated, relative to the tubular sleeve, in the direction of the spiral guide track, thereby extending the injection needle out of the bottom end of the tubular sleeve; and
   f) a lateral guide track on the interior wall of the tubular sleeve connecting the spiral guide track to a vertical guide track on the interior wall of the tubular sleeve, wherein the guide pin is constructed to move from the spiral guide track through the lateral guide track to the vertical guide track when the syringe barrel is further rotated in the direction of the spiral guide track and wherein the injection needle is retracted into the interior of the tubular sleeve when the guide pin is moved into the vertical guide track and moved upwards in the vertical guide track towards a top end of the tubular sleeve.

2. The single dose disposable syringe of claim 1, further comprising a retaining slot at a top end and at a bottom end of the spiral guide track and at a top end of the vertical track to retain the guide pin.

3. The single dose disposable syringe of claim 1, further comprising a biasing member on the injection needle to bias the guide member upwards in the vertical guide track, wherein the biasing member is a spring mounted on a base of the injection needle.

4. The single dose disposable syringe of claim 1, wherein the guide pin in the spiral guide track moves from a top end of the spiral guide track to a bottom end of the spiral guide track.

5. The single dose disposable syringe of claim 2, further comprising the retaining slot at the bottom end of the spiral guide track being constructed to prevent a reverse in rotation of the syringe barrel.

6. The single dose disposable syringe of claim 1, further comprising a finger grip on the syringe barrel at a top end of the syringe barrel.

7. A single dose disposable syringe having a tubular sleeve protector, said syringe comprising:
   a) a syringe barrel, a plunger, and an injection needle attached to the syringe barrel;
   b) a guide pin on an exterior side of the syringe barrel;
   c) the syringe barrel and the injection needle positioned in an interior of a tubular sleeve, the tubular sleeve having a first side and a second side radially opposite the first side;
   d) the tubular sleeve having a spiral guide track on an interior wall of the tubular sleeve, the spiral guide track making only a single spiral turn from the first side to the second side on the interior wall of the tubular sleeve;
   e) the guide pin constructed to fit in the spiral guide track and to move the syringe barrel towards a bottom end of the tubular sleeve as the syringe barrel is rotated, relative to the tubular sleeve, in the direction of the spiral guide track, thereby extending the injection needle out of the bottom end of the tubular sleeve;
   f) a lateral guide track on the interior wall of the tubular sleeve connecting the spiral guide track to a vertical guide track on the interior wall of the tubular sleeve, wherein the guide pin is constructed to move from the spiral guide track through the lateral guide track to the vertical guide track when the syringe barrel is further rotated in the direction of the spiral guide track and wherein the injection needle is retracted into the interior of the tubular sleeve when the guide pin is moved into the vertical guide track and moved upwards in the vertical guide track towards a top end of the tubular sleeve; and
   g) a retaining slot at a top end and at a bottom end of the spiral guide track and at a top end of the vertical track to retain the guide pin.

8. The single dose disposable syringe of claim 7, further comprising a biasing member on the injection needle to bias the guide member upwards in the vertical guide track, wherein the biasing member is a spring mounted on a base of the injection needle.

9. The single dose disposable syringe of claim 7, wherein the guide pin in the spiral guide track moves from the top end of the spiral guide track to the bottom end of the spiral guide track.

10. The single dose disposable syringe of claim 7, further comprising the retaining slot at the second opposite end of the spiral guide track being constructed to prevent a reverse in rotation of the syringe barrel.

11. The single dose disposable syringe of claim 7, further comprising a finger grip on the syringe barrel at a top end of the syringe barrel.

12. A single dose disposable syringe having a tubular sleeve protector, said syringe comprising:
   a) a syringe barrel, a plunger, and an injection needle attached to the syringe barrel;
   b) a guide pin on an exterior side of the syringe barrel;
   c) the syringe barrel and the injection needle positioned in an interior of a tubular sleeve, the tubular sleeve having a first side and a second side radially opposite the first side;
   d) the tubular sleeve having a spiral guide track on an interior wall of the tubular sleeve, the spiral guide track making a only single spiral turn from the first side to the second side on the interior wall of the tubular sleeve;
   e) the guide pin constructed to fit in the spiral guide track and to move the syringe barrel towards a bottom end of the tubular sleeve as the syringe barrel is rotated, relative to the tubular sleeve, in the direction of the spiral guide track, thereby extending the injection needle out of the bottom end of the tubular sleeve;
   f) a lateral guide track on the interior wall of the tubular sleeve connecting the spiral guide track to a vertical guide track on the interior wall of the tubular sleeve, wherein the guide pin is constructed to move from the spiral guide track through the lateral guide track to the vertical guide track when the syringe barrel is further rotated in the direction of the spiral guide track and wherein the injection needle is retracted into the interior of the tubular sleeve when the guide pin is moved into the vertical guide track and moved upwards in the vertical guide track towards a top end of the tubular sleeve;
   g) a retaining slot at a top end and at a bottom end of the spiral guide track and at a top end of the vertical track to retain the guide pin; and
   h) a biasing member on the injection needle to bias the guide member upwards in the vertical guide track, wherein the biasing member is a spring mounted on a base of the injection needle.

13. The single dose disposable syringe of claim 12, wherein the guide pin in the spiral guide track moves from the top end of the spiral guide track to the bottom end of the spiral guide track.

14. The single dose disposable syringe of claim 12, further comprising the retaining slot at the bottom end of the spiral guide track being constructed to prevent a reverse in rotation of the syringe barrel.

15. The single dose disposable syringe of claim 12, further comprising a finger grip on the syringe barrel at a top end of the syringe barrel.

16. A single dose disposable syringe having a tubular sleeve protector, said syringe comprising:
   a) a syringe barrel, a plunger, and an injection needle attached to the syringe barrel;
   b) a guide pin on an exterior side of the syringe barrel;
   c) the syringe barrel and the injection needle positioned in an interior of a tubular sleeve, the tubular sleeve having a first side and a second side radially opposite the first side;
   d) the tubular sleeve having a spiral guide track on an interior wall of the tubular sleeve, the spiral guide track making only a single spiral turn from the first side to the second side on the interior wall of the tubular sleeve;
   e) the guide pin constructed to fit in the spiral guide track and to move the syringe barrel towards a bottom end of the tubular sleeve as the syringe barrel is rotated, relative to the tubular sleeve, in the direction of the spiral guide track, thereby extending the injection needle out of the bottom end of the tubular sleeve;
   f) a lateral guide track on the interior wall of the tubular sleeve connecting the spiral guide track to a vertical guide track on the interior wall of the tubular sleeve, wherein the guide pin is constructed to move from the spiral guide track through the lateral guide track to the vertical guide track when the syringe barrel is further rotated in the direction of the spiral guide track and wherein the injection needle is retracted into the interior of the tubular sleeve when the guide pin is moved into the vertical guide track and moved upwards in the vertical guide track towards a top end of the tubular sleeve;
   g) a retaining slot at a top end and at a bottom end of the spiral guide track and at a top end of the vertical track to retain the guide pin;
   h) a biasing member on the injection needle to bias the guide member upwards in the vertical guide track, wherein the biasing member is a spring mounted on the hub of the injection needle; and
   i) the retaining slot at the bottom end of the spiral guide track being constructed to prevent a reverse in rotation of the syringe barrel.

17. The single dose disposable syringe of claim 16, wherein the guide pin in the spiral guide track moves from the top end of the spiral guide track to the bottom end of the spiral guide track.

18. The single dose disposable syringe of claim 16, further comprising a finger grip on the syringe barrel at a top end of the syringe barrel.

19. A method of protecting a syringe needle on a single dose disposable syringe, the method comprising:
   1) providing a syringe having a syringe barrel, a plunger, and an injection needle;
   2) providing a guide pin on an exterior side of the syringe barrel;
   3) positioning the syringe barrel and injection needle inside a tubular sleeve, the tubular sleeve having a first side and a second side radially opposite the first side, the tubular sleeve having a spiral guide track, a lateral guide track, and a vertical guide track on an interior wall of the tubular sleeve, wherein the guide pin fits into the spiral guide track, the lateral guide track, and the vertical guide track and wherein the spiral guide track makes only a single spiral turn from the first side to the second side on the interior wall of the tubular sleeve;
   4) extending the syringe needle out from a bottom end of the tubular sleeve by rotating the syringe barrel, relative to the tubular sleeve, in the direction of the spiral guide track and by moving the guide pin from a top end of the spiral guide track to a bottom end of the spiral guide track, thereby moving the syringe barrel and injection needle towards the bottom end of the tubular sleeve; and
   5) retracting the injection needle back into the tubular sleeve by further rotating the syringe barrel, relative to the tubular sleeve, in the direction of the spiral guide track and by moving the guide pin across the lateral guide track and into the vertical guide track and moving the guide pin upwards in the vertical guide track towards a top end of the tubular sleeve, thereby moving the syringe barrel and syringe needle towards the top end of the tubular sleeve.

20. The method of claim 19, wherein the top end and the bottom end of the spiral guide track and a top end of the vertical track have a retaining slot to retain the guide pin.

21. The method of claim 19, wherein the injection needle has a biasing member to bias the guide member upwards in the vertical guide track and wherein the biasing member is a spring mounted on a base of the injection needle.

22. The method of claim 20, wherein the retaining slot at the bottom end of the spiral guide track is constructed to prevent a reverse in rotation of the syringe barrel.

23. The method of claim 19, wherein the syringe barrel has a finger grip at a top end of the syringe barrel.

24. A method of protecting a syringe needle on a single dose disposable syringe, the method comprising:
   1) providing a syringe having a syringe barrel, a plunger, and an injection needle;
   2) providing a guide pin on an exterior side of the syringe barrel;
   3) positioning the syringe barrel and injection needle inside a tubular sleeve, the tubular sleeve having a first side and a second side radially opposite the first side, the tubular sleeve having a spiral guide track, a lateral guide track, and a vertical guide track on an interior wall of the tubular sleeve, wherein the guide pin fits into the spiral guide track, the lateral guide track, and the vertical guide track and wherein the spiral guide track makes only a single spiral turn from the first side to the second side on the interior wall of the tubular sleeve;
   4) extending the syringe needle out from a bottom end of the tubular sleeve by rotating the syringe barrel, relative to the tubular sleeve, in the direction of the spiral guide track and by moving the guide pin from a top end of the spiral guide track to a bottom end of the spiral guide track, thereby moving the syringe barrel and injection needle towards the bottom end of the tubular sleeve; and
   5) retracting the injection needle back into the tubular sleeve by further rotating the syringe barrel, relative to the tubular sleeve, in the direction of the spiral guide track and by moving the guide pin across the lateral guide track and into the vertical guide track and moving the guide pin upwards in the vertical guide track towards a top end of the tubular sleeve, thereby moving the syringe barrel and syringe needle towards the top end of the tubular sleeve;
   wherein the top end and the bottom end of the spiral guide track and a top end of the vertical track have a retaining slot to retain the guide pin.

25. The method of claim 24, wherein the injection needle has a biasing member to bias the guide member upwards in the vertical guide track and wherein the biasing member is a spring mounted on a base of the injection needle.

26. The method of claim 24, wherein the retaining slot at the bottom end of the spiral guide track is constructed to prevent a reverse in rotation of the syringe barrel.

27. The method of claim 24, wherein the syringe barrel has a finger grip at a top end of the syringe barrel.

28. A method of protecting a syringe needle on a single dose disposable syringe, the method comprising:
   1) providing a syringe having a syringe barrel, a plunger, and an injection needle;
   2) providing a guide pin on an exterior side of the syringe barrel;
   3) positioning the syringe barrel and injection needle inside a tubular sleeve, the tubular sleeve having a first side and a second side radially opposite the first side, the tubular sleeve having a spiral guide track, a lateral guide track, and a vertical guide track on an interior wall of the tubular sleeve, wherein the guide pin fits into the spiral guide track, the lateral guide track, and the vertical guide track and wherein the spiral guide track makes only a single spiral turn from the first side to the second side on the interior wall of the tubular sleeve;
   4) extending the syringe needle out from a bottom end of the tubular sleeve by rotating the syringe barrel, relative to the tubular sleeve, in the direction of the spiral guide track and by moving the guide pin from a top end of the spiral guide track to a bottom end of the spiral guide track, thereby moving the syringe barrel and injection needle towards the bottom end of the tubular sleeve; and
   5) retracting the injection needle back into the tubular sleeve by further rotating the syringe barrel, relative to the tubular sleeve, in the direction of the spiral guide track and by moving the guide pin across the lateral guide track and into the vertical guide track and moving the guide pin upwards in the vertical guide track towards a top end of the tubular sleeve, thereby moving the syringe barrel and syringe needle towards the top end of the tubular sleeve;
   wherein the top end and the bottom end of the spiral guide track and a top end of the vertical track have a retaining slot to retain the guide pin,
   wherein the injection needle has a biasing member to bias the guide member upwards in the vertical guide track, and
   wherein the biasing member is a spring mounted on a base of the injection needle.

29. The method of claim 28, wherein the retaining slot at the bottom end of the spiral guide track is constructed to prevent a reverse in rotation of the syringe barrel.

30. The method of claim 29, wherein the syringe barrel has a finger grip at a top end of the syringe barrel.

* * * * *